US012734179B2

(12) United States Patent
Diamond et al.

(10) Patent No.: US 12,734,179 B2
(45) Date of Patent: Sep. 15, 2026

(54) PROGESTERONE FORMULATION TO TRIGGER OVULATION AND PROVIDE LUTEAL PHASE SUPPORT

(71) Applicants: AUGUSTA UNIVERSITY RESEARCH INSTITUTE, INC., Augusta, GA (US); Vitrovita LLC, Houston, TX (US)

(72) Inventors: Michael Peter Diamond, Grosse Pointe Shores, MI (US); Dmitri Dozortsev, Houston, TX (US)

(73) Assignees: AUGUSTA UNIVERSITY RESEARCH INSTITUTE, INC., Augusta, GA (US); Vitrovita LLC, Houston, TX (US)

( * ) Notice: Subject to any disclaimer, the term of this patent is extended or adjusted under 35 U.S.C. 154(b) by 1120 days.

(21) Appl. No.: 17/757,882

(22) PCT Filed: Apr. 14, 2020

(86) PCT No.: PCT/US2020/028121
§ 371 (c)(1),
(2) Date: Jun. 22, 2022

(87) PCT Pub. No.: WO2021/133430
PCT Pub. Date: Jul. 1, 2021

(65) Prior Publication Data

US 2023/0044690 A1 Feb. 9, 2023

Related U.S. Application Data

(60) Provisional application No. 62/952,539, filed on Dec. 23, 2019.

(51) Int. Cl.
*A61K 31/57* (2006.01)
*A61K 9/00* (2006.01)
(Continued)

(52) U.S. Cl.
CPC ............ *A61K 31/57* (2013.01); *A61K 9/0019* (2013.01); *A61K 9/0024* (2013.01);
(Continued)

(58) Field of Classification Search
CPC .... A61K 31/57; A61K 9/0024; A61K 9/0034; A61K 31/196; A61K 9/0053; A61K 9/0036
See application file for complete search history.

(56) References Cited

U.S. PATENT DOCUMENTS

2001/0029357 A1 10/2001 Bunt et al.
2005/0065080 A1 3/2005 Barkan et al.
2006/0217315 A1 9/2006 Coelingh Bennink et al.
(Continued)

FOREIGN PATENT DOCUMENTS

JP 2001-523515 A 11/2001
WO 99/26556 A1 6/1999
WO 2013/029194 A1 3/2013
WO 2021/133430 A1 7/2021

OTHER PUBLICATIONS

Zalányi, European Journal of Obstetrics & Gynecology and Reproductive Biology, vol. 98, Issue 2, Oct. 2001, pp. 152-159 (Year: 2001).*

(Continued)

*Primary Examiner* — San Ming R Hui
(74) *Attorney, Agent, or Firm* — Pabst Patent Group LLP

(57) ABSTRACT

Disclosed herein are compositions and methods for ovulation induction in females in need thereof. Current methods for inducing ovulation have unpleasant side effects and are expensive. The disclosed compositions and methods are safe, efficacious, and inexpensive. An exemplary method of inducing ovulation includes steps of monitoring ovarian follicle development and size during the follicular phase of the menstrual cycle; and administering to the subject a
(Continued)

pharmaceutical composition including progesterone or bioidentical progesterone in an amount effective to increase the plasma concentration of progesterone to between about 0.1 ng/ml to about 1 ng/ml when the follicle reaches a size of at least 15 mm.

23 Claims, 9 Drawing Sheets

(51) Int. Cl.

| | |
|---|---|
| ***A61K 9/02*** | (2006.01) |
| ***A61K 31/138*** | (2006.01) |
| ***A61K 31/196*** | (2006.01) |
| ***A61K 31/4196*** | (2006.01) |
| ***A61K 38/09*** | (2006.01) |
| ***A61P 15/08*** | (2006.01) |

(52) U.S. Cl.
CPC .............. *A61K 9/0034* (2013.01); *A61K 9/02* (2013.01); *A61K 31/138* (2013.01); *A61K 31/196* (2013.01); *A61K 31/4196* (2013.01); *A61K 38/09* (2013.01); *A61P 15/08* (2018.01)

(56) References Cited

U.S. PATENT DOCUMENTS

| | | | | |
|---|---|---|---|---|
| 2009/0137478 | A1* | 5/2009 | Bernstein .................. | A61P 5/24 514/1.1 |
| 2010/0272779 | A1 | 10/2010 | Jackson | |
| 2018/0289614 | A1 | 10/2018 | Colman et al. | |

OTHER PUBLICATIONS

International Search Report issued in PCT/US2020/028121 on Jul. 24, 2020 (2 pages).

Written Opinion issued in PCT/US2020/028121 on Jul. 24, 2020 (2 pages).

Office Action received for Japanese Patent Application No. 2022-563856, mailed on Dec. 3, 2024, 6 pages (3 pages of English Translation and 3 pages of Original Document).

International Preliminary Report on Patentability received for PCT Patent Application No. PCT/US20/28121, mailed on Jul. 7, 2022, 8 pages.

Office Action received for Japanese Patent Application No. 2022-563856, mailed on May 7, 2024, 9 pages (5 pages of English Translation and 4 pages of Original Document).

Tabira et al., "Cooperative action of progesterone and prostaglandins in the ovulation regulatoin mechanism", Advances in Obstetrics and Gynecology, vol. 35, No. 2, 1983, pp. 125-129.

* cited by examiner

General
Freq 6.0M
Depth 6.0cm
Sector 100%
Gain 45%
FrRate Med
FPS 38Hz
Dyn 68dB
Persist3
Map3 Chr1
SoS 1540m/s
Power 0
MI<0.88
TIS<0.15
Clarity High
Zoom 100%

General
Freq 6.0M
Depth 6.0cm
Sector 100%
Gain 45%
FrRate Med
FPS 38Hz
Dyn 68dB
Persist3
Map3 Chr1
SoS 1540m/s
Power 0
MI<0.88
TIS<0.15
Clarity High
Zoom 100%

PROGESTERONE FORMULATION TO TRIGGER OVULATION AND PROVIDE LUTEAL PHASE SUPPORT

CROSS-REFERENCE TO RELATED APPLICATIONS

The present invention is filed under 35 U.S.C. § 371 as the U.S. national phase of International Application No. PCT/US2020/028121, filed Apr. 14, 2020, which designated the U.S. and claims priority to and benefit of U.S. Provisional Application No. 62/952,539 filed on Dec. 23, 2019, each of which is incorporated by reference in its entirety.

TECHNICAL FIELD OF THE INVENTION

This invention is generally related to compositions and methods of inducing ovulation and treating infertility.

BACKGROUND OF THE INVENTION

The female menstrual cycle can be functionally divided into three phases: the follicular phase, the ovulatory phase, and the luteal phase. The follicular period begins at the end of the luteal phase of the preceding non-conceptive menstrual cycle, prior to or coincident with the onset of menses. Cycle initiation is preceded with a transient rise in blood levels of FSH that stimulates development of a cohort of ovarian follicles. Each follicle houses an immature egg. The size of the follicles recruited to grow is about 15 mm in diameter. In a natural menstrual cycle, usually one large or dominant follicle is established during the follicular phase, and it is committed to growth to maturation. In humans, the size of the follicle that is considered ready to ovulate is about 15 mm or more in diameter. Granulosa cells within the ovarian follicles acquire receptors for LH and become increasingly responsive to LH. Secretion of estradiol and estrone from the ovary increases slowly at first, in parallel to the increasing diameter of the follicle and sensitivity of the follicle to LH.

Ovulation is the second phase of the ovarian cycle in which a mature egg is released from the ovarian follicles into the oviduct. The timing of ovulation within the female menstrual cycle is critical to fertilization. During the follicular phase, estradiol suppresses release of luteinizing hormone (LH) from the anterior pituitary gland. When the egg has nearly matured, levels of estradiol reach a threshold above which this effect is reversed and estrogen stimulates the production of a large amount of LH. This process, known as the LH surge, starts around day 12 of the average cycle and may last 48 hours. The release of LH matures the egg and weakens the wall of the follicle in the ovary, causing the fully developed follicle to release its secondary oocyte. The egg is funneled into the fallopian tube and toward the uterus by waves of small, hair-like projections. If it is fertilized by a sperm, the secondary oocyte promptly matures into an ootid and then becomes a mature ovum. If it is not fertilized by a sperm, the secondary oocyte will degenerate. The mature ovum has a diameter of about 0.2 mm.

Triggering ovulation is a crucial step in the management of the controlled ovarian stimulation in patients undergoing IVF, IUI, timed intercourse, and other forms of fertility therapy. The ovulation trigger is not only ultimately responsible for the last stages of oocyte maturation and follicle's rupture, but also primes the endometrium for subsequent implantation. Currently hCG is the only medication specifically approved by the FDA as an ovulation trigger. However, its use is rapidly declining due to the relatively high incidence of ovarian hyperstimulation syndrome (OHHS). Lupron Acetate is increasingly used as an off-label ovulation drug of choice due to its low incidence of OHHS and a generally good record of safety and efficacy. However, Lupron is expensive and has several unpleasant side effects. Thus, there is a need for a safe, effective, and low cost alternative for triggering ovulation in women in need thereof.

It is an object of the invention to provide compositions and methods for triggering ovulation in a subject in need thereof.

It is also an object of the invention to provide methods of treating infertility in a subject in need thereof.

SUMMARY OF THE INVENTION

Disclosed herein are compositions and methods for inducing ovulation in females in need thereof. Current methods for inducing ovulation have unpleasant side effects and are expensive. The disclosed compositions and methods are safe, efficacious, and inexpensive. An exemplary method of inducing ovulation includes steps of monitoring ovarian follicle development and size during the follicular phase of the menstrual cycle; and administering to the subject a pharmaceutical composition including progesterone or bioidentical progesterone in an amount effective to increase the plasma concentration of progesterone to between about 0.1 ng/ml to about 1 ng/ml when the follicle reaches a size of at least 15 mm. In one embodiment, the administration of progesterone to the subject induces luteinizing hormone (LH) surge and subsequent ovulation in the subject.

In another embodiment, the subject's baseline plasma progesterone concentration is determined prior to administering progesterone. This baseline plasma progesterone concentration is used to calculate the target maximum progesterone concentration for the subject, wherein the target concentration is calculated by multiplying the baseline level by a number from 3 to 20.

In some embodiments, the subject can also be administered additional fertility therapeutics such as GnRH antagonists, selective estrogen receptor modulators, anti-inflammatory agents, and non-steroidal aromatase inhibitors.

Another embodiment provides a method for controlling luteinizing hormone (LH) release and ovulation during a menstrual cycle including the steps of a) administering to the subject an estrogen modulator for several days during the follicular phase; b) administering to the subject an anti-inflammatory drug for several days during the follicular phase; c) monitoring ovarian follicle development and size throughout the follicular phase of the menstrual cycle; and d) administering progesterone or progestin to the subject in an amount effective to increase plasma concentration of progesterone to between about 0.1 ng/ml to about 1.0 ng/ml when the follicle reaches a size of at least 15 mm, wherein the progesterone induces LH surge and ovulation in the subject.

The estrogen modulator is a GnRH antagonist, a non-steroidal aromatase inhibitor, or a selective estrogen receptor modulator. The estrogen modulator is administered for about 3 to 5 days beginning on the third to fifth day from the start of the subject's menstrual period. The anti-inflammatory drug is a non-steroidal anti-inflammatory drug. The anti-inflammatory drug is administered at least one day prior to administration of the pharmaceutical composition comprising progesterone.

In some embodiments, the subject can also be administered additional fertility therapeutics such as GnRH antagonists, selective estrogen receptor modulators, anti-inflammatory agents, and non-steroidal aromatase inhibitors.

The pharmaceutical compositions used in the disclosed methods can be formulated for oral, intravenous, subcutaneous, intramuscular, transvaginal, or rectal administration. The amount of progesterone in the pharmaceutical composition formulated for oral administration is between about 5 mg to about 30 mg. The amount of progesterone in the pharmaceutical composition formulated for intramuscular administration is between about 1 mg to about 3 mg. The administration of progesterone to the subject can be repeated several times over a period of about 4 hours to about 12 hours. Progesterone can be administered to the subject daily for at least one day following the initial administration of progesterone, wherein the daily progesterone is begun at least three days after the initial administration.

Also described is a controlled release pharmaceutical implant including a controlled release polymeric implant having progesterone or bioidentical progesterone, wherein the implant releases a steady level of progesterone in an amount effective to increase plasma concentration of progesterone to between about 0.1 ng/ml to about 1.0 ng/ml for at least 5 days. The implant is designed to be subcutaneously implanted into the arm of a subject. In another embodiment, the implant is designed to be implanted into the uterine lining of a subject, or placed in the uterine cavity.

The disclosed methods and compositions are useful for triggering ovulation in subjects with a desire for controlled ovarian stimulation and/or ovulation, as well as subjects with infertility or reduced infertility caused by ovulation problems, endometriosis, poor egg quality, polycystic ovarian syndrome (PCOS), fallopian tube problems, unexplained infertility, poor sperm quality, advanced age, or premature ovarian insufficiency.

BRIEF DESCRIPTION OF THE DRAWINGS

FIG. 1A shows hormone interplay around ovulation, while FIG. 1B shows the hypothalamic-pituitary-gonadal axis.

DETAILED DESCRIPTION OF THE INVENTION

I. Definitions

Figure 1A:
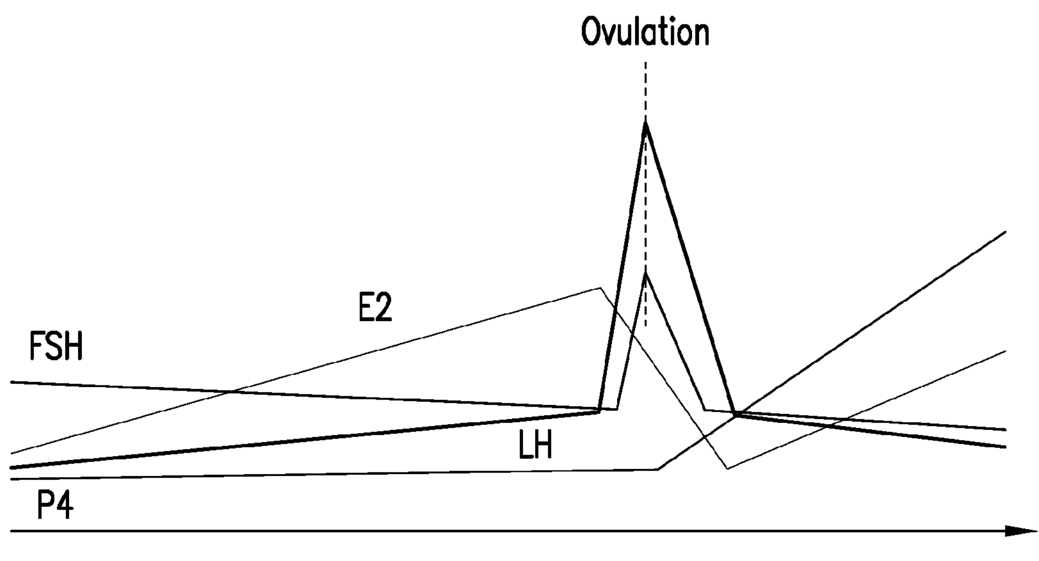
FIG. 1A-1B are schematic illustrations of the current ovulation paradigm.
Figure 1B:
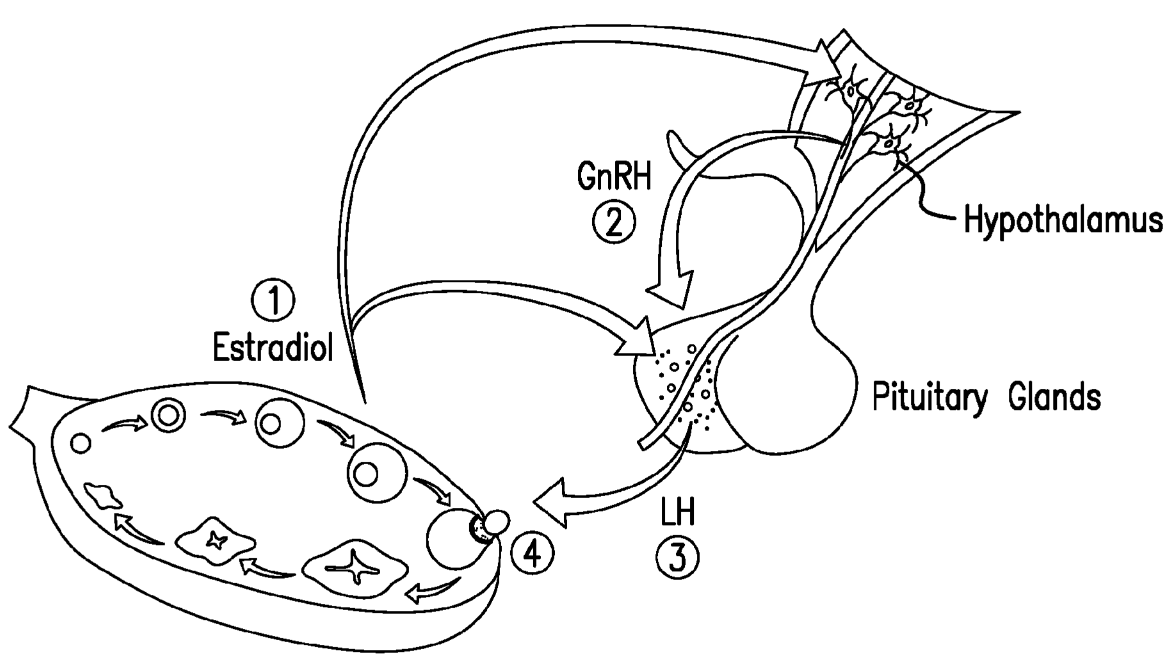
Figure 2:
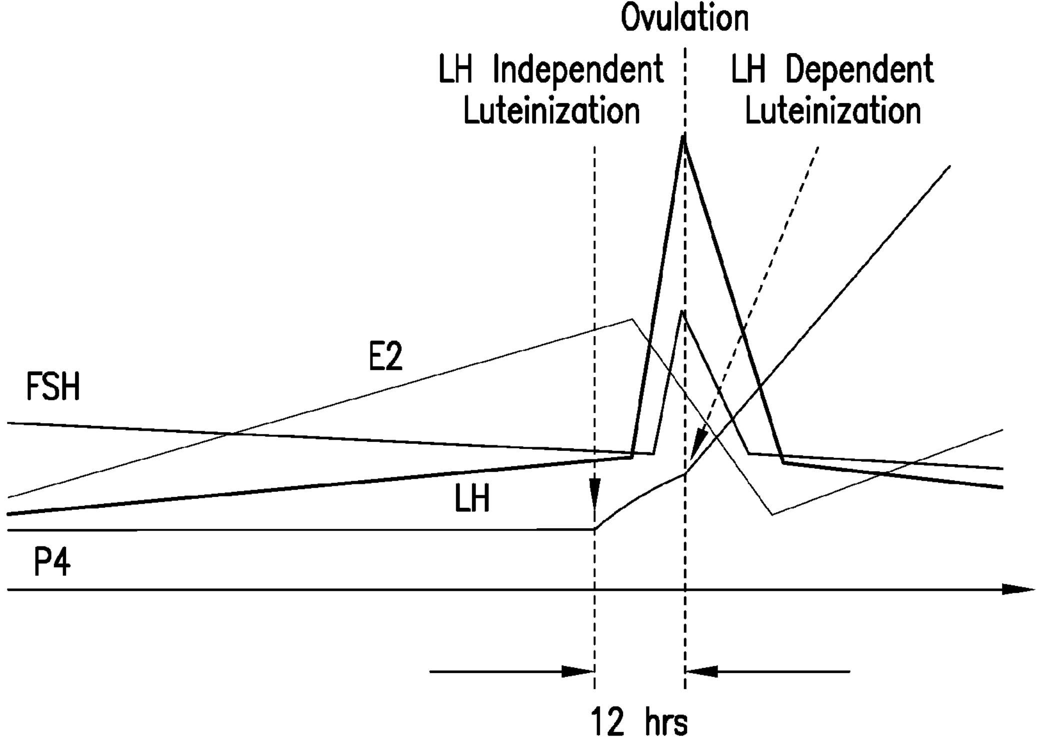
FIG. 2 is a schematic of the proposed ovulation paradigm.
Figure 3:
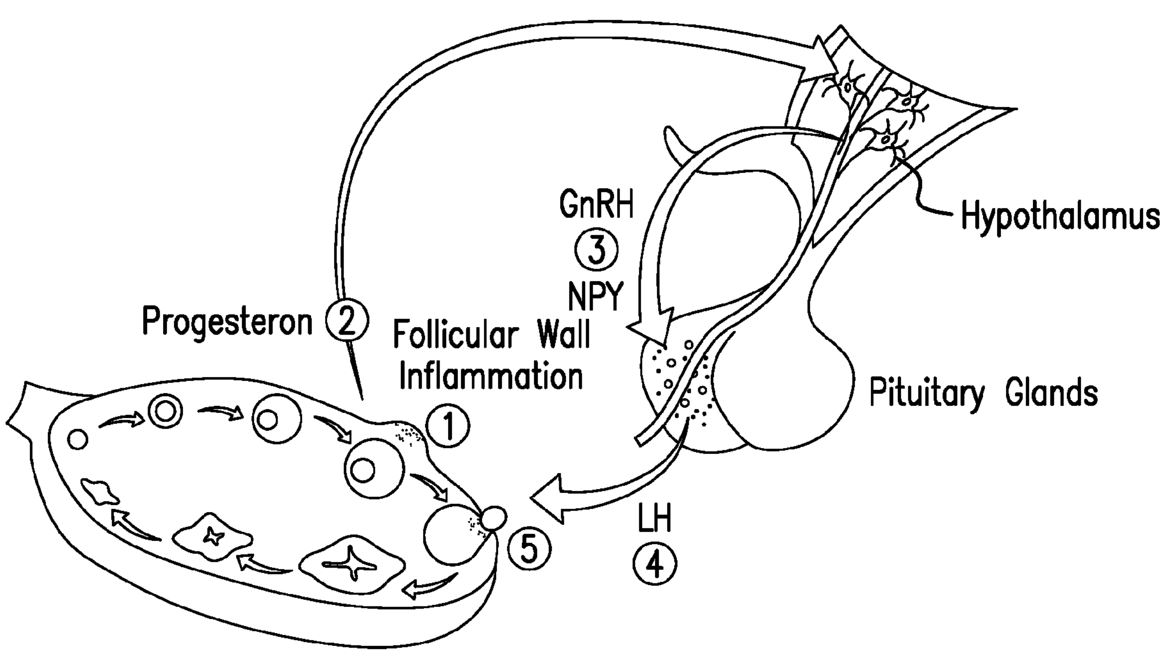
FIG. 3 is a schematic illustration of the proposed ovulation sequence. As the follicle begins to lose integrity (1) due to inflammation, some granulosa cells luteinize, leading to increase in circulating progesterone of about 0.5 ng/ml (2), which invokes the surge of GnRH and NPY (3). NPY selectively increases sensitivity of LH containing granins (Bauer-Dantoinet al, 1993) to GnRH resulting in preferential surge of LH (4), which causes the follicle to rupture and egg to ovulate (5).

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein the terms "estradiol" and "E2" can be used interchangeably and refer to an estrogen steroid hormone. It is a major female sex hormone that is involved in the regulation of the estrous and menstrual female reproductive cycles. Estradiol is produced within the follicles of the ovaries, but can be produced by testicles, adrenal glands, fat, liver, the breasts and the brain.

As used herein, the terms "progesterone" and "P4" can be used interchangeably and refer to an endogenous steroid and progestogen sex hormone involved in the menstrual cycle, pregnancy and embryogenesis. It belongs to the group of steroid hormones called the progestogens.

As used herein, the terms "gonadotropin releasing hormone" and "GnRH" can be used interchangeably and refer to a releasing hormone that is responsible for the release of follicle-stimulating hormone (FSH) and luteinizing hormone (LH) from the anterior pituitary. GnRH is a tropic peptide hormone synthesized and released from GnRH neurons within the hypothalamus.

As used herein, the terms "luteinizing hormone", "LH" and "lutropin" can be used interchangeably and refer to a hormone produced by gonadotropic cells in the anterior pituitary gland. In females, an acute rise in LH (referred to as the LH surge) triggers ovulation and development of the corpus luteum.

As used herein, the terms "follicle-stimulating hormone" and "FSH" can be used interchangeably and refer to a gonadotropin, more specifically a glycoprotein polypepetide hormone. FSH is synthesized and secreted by the gonadotropic cells of the anterior pituitary gland, and regulates the development, growth, pubertal maturation, and reproductive processes of the body. FSH and LH work together in the reproductive system.

As used herein, the term "in vitro fertilization" and "IVF" can be used interchangeably and refer to a process of fertilization in which an egg is combined with a sperm outside of the body. The process involves monitoring and stimulating a woman's ovulatory process, removing an egg or eggs from the woman's ovaries and letting sperm fertilize them in a liquid in a laboratory. After the fertilized egg undergoes embryo culture for 2-6 days, it is implanted in the same or another woman's uterus, with the intention of establishing a successful pregnancy. While IVF can be performed by collecting eggs directly from the fallopian tubes after natural ovulation, it is typically combined with other techniques that increase the likelihood of a successful pregnancy. These techniques include but are not limited to ovarian hyperstimulation to generate multiple eggs, ultrasound-guided transvaginal oocyte retrieval directly from the ovaries, co-incubation of eggs and sperm, as well as culture and selection of resultant embryos before embryo transfer into a uterus.

As used herein, the term "intracytoplasmic sperm injection" and "ICSI" can be used interchangeably and refer to an IVF treatment in which a single sperm cell is injected directly into the cytoplasm of an egg. ICSI differs from IVF in that ICSI needs one only sperm cell per egg, meanwhile IVF needs between 50,000 and 100,000 sperm cells.

As used herein, the term "ovarian follicle" and "follicle" can be used interchangeable and refer to a fluid-filled sac that contains an immature egg. An ovarian follicle is unique in its function, yet it is closely related to hair follicle. Similarly, to the hair follicle, it has a predictable life-cycle and it will rupture at the end, expelling its content. The hair follicle expels a hair (Rosenfield and Lucky, 1993), while the ovarian follicle expels the egg.

II. Methods of Triggering Ovulation

Disclosed herein are methods and compositions for triggering ovulation. Triggering ovulation is a crucial step in the management of the controlled ovarian stimulation in patients undergoing IVF, IUI, timed intercourse, and other forms of fertility therapy. The ovulation trigger is not only ultimately responsible for the last stages of oocyte maturation and follicle's rupture, but also primes the endometrium for subsequent implantation. Currently hCG is the only medication specifically approved by FDA as an ovulation trigger. However, its use is rapidly declining due to the relatively high incidence of the ovarian hyperstimulation syndrome (OHHS). Lupron acetate is increasingly used an off-label ovulation drug of choice due to its low incidence of OHHS and a generally good record of safety and efficiency. Yet, lupron is expensive and has a several unpleasant side effects.

Several derivatives of Kisspeptin are in the process of investigation (Phase II), but are expected to be on the expensive side, should they reach the market (Abbara et al, 2017). The important shortcoming of all currently available triggers, including Kisspeptin, is their inability to fully reproduce the naturally occurring pulsating pattern of GnRH release, which is believed to be a consequential feature of the process. In order to compensate for this deficiency, Kisspeptin, for example, has to be injected several times. Also, in order to mimic the pulsating nature of GnRH release, a successful use of the pump has been reported (Zheng J et al, 2017). Neither is clinically practical for a general infertility population.

These treatments are based on the currently accepted ovulation paradigm that postulates E2's rise into the range of above 200-300 pg/ml for a minimum of 50 hours is what triggers GnRH release, which in turn binds to its receptors in the anterior hypophysis, causing the release of LH and FSH into the circulation and culminating in the rupture of the follicle (Christensen et al, 2012). However, it has been discovered that under physiological conditions, there are two waves of progesterone. The first wave is an LH-independent, precipitous rise of progesterone 12 hours before gonadotropins surge to about 0.5 ng/ml that signals to the hypothalamus that a follicle is ready to rupture. This rise activates GnRH signaling pathway, with an ensuing LH/FSH surge which causes the follicle to rupture and its granulose to luteinize. The preovulatory peak of progesterone is seemingly small, of only about 0.5 ng/ml, compared to postovulatory peak which is about ten time higher. The relatively low level of the preovulatory peak makes it difficult to recognize its significance as an ovulation trigger. However, it has been discovered that administration of progesterone to a woman after the ovarian follicle has reached a threshold size induces ovulation, even if the woman has been diagnosed with infertility problems.

A. Ovulation Induction Regimen

Disclosed herein are methods for inducing ovulation in a subject in need thereof by administering progesterone to the subject during the follicular phase of the menstrual cycle. An exemplary method includes steps of a) monitoring ovarian follicle development and size during the follicular phase of the menstrual cycle, and b) administering to the subject a pharmaceutical composition including progesterone or bioidentical progesterone in an amount effective to increase the plasma concentration of progesterone to between about 0.1 ng/ml to about 100 ng/ml when the follicle reaches a size of at least 15 mm. Without being bound to any one theory, it is believed that increasing the plasma concentration of progesterone once the follicle has reached a mature size triggers LH surge causing the follicle to rupture and release the egg.

In some embodiments, the subject's plasma progesterone levels are monitored throughout the follicular phase in order to calculate the target level of progesterone to be achieved for triggering ovulation.

Another method includes steps of a) administering to the subject a non-steroidal or steroid anti-inflammatory drug for several days during the follicular phase, b) administering to the subject GnRH antagonist for at least one day in the second part of the follicular phase, c) monitoring ovarian follicle development and size during the follicular phase of the menstrual cycle, and d) administering progesterone or progestin to the subject in an amount effective to increase plasma concentration of progesterone to between about 0.1 ng/ml to about 1.0 ng/ml when the follicle reaches a size of at least 15 mm, wherein the progesterone induces LH surge and ovulation in the subject.

More detailed descriptions of the methods and compositions are provided below.

1. Follicular Phase and Ovulation

In one embodiment, the disclosed methods occur during the follicular phase of a subject's menstrual cycle. The follicular phase begins at the end of the luteal phase of the preceding non-conceptive menstrual cycle, prior to or coincident with the onset of menses. The cycle starts with a transient rise in blood levels of FSH that stimulates development of a cohort of ovarian follicles. Each follicle houses an immature egg. The size of the follicles recruited to grow is about 5 mm in diameter. In a natural menstrual cycle, usually one large or dominant follicle is established during the follicular phase, and it is committed to growth to maturation. In humans, the size of the follicle that is considered ready to ovulate is about 15 mm or more in diameter. Granulosa cells within the ovarian follicles acquire receptors for LH and become increasingly responsive to LH. Secretion of estradiol and estrone from the ovary increases slowly at first, in parallel to the increasing diameter of the follicle and sensitivity of the follicle to LH.

In one embodiment, the progesterone treatment is administered when the follicle has reached a size of at least 15 mm in diameter. In another embodiment, the follicle is 15 mm in diameter to 30 mm in diameter. The follicle can be 15 mm, 15.5 mm, 16 mm, 16.5 mm, 17 mm, 17.5 mm, 18 mm, 18.5 mm, 19 mm, 19.5 mm, 20 mm, 21 mm, 22 mm, 23 mm, 24 mm, 25 mm, 26 mm, 27 mm, 28 mm, 29 mm, or 30 mm.

In one embodiment, administration of progesterone to the subject when the follicle reaches a threshold size triggers ovulation by inducing an LH surge. Ovulation is the second phase of the ovarian cycle in which a mature egg is released from the ovarian follicles into the oviduct. During the follicular phase, estradiol suppresses release of luteinizing hormone (LH) from the anterior pituitary gland. When the egg has nearly matured, levels of estradiol reach a threshold above which this effect is reversed and estrogen stimulates the production of a large amount of LH. This process, known as the LH surge, starts around day 12 of the average cycle and may last 48 hours. The release of LH matures the egg and weakens the wall of the follicle in the ovary, causing the fully developed follicle to release its secondary oocyte. The egg is funneled into the fallopian tube and toward the uterus by waves of small, hair-like projections. If it is fertilized by a sperm, the secondary oocyte promptly matures into an ootid and then becomes a mature ovum. If it is not fertilized by a sperm, the secondary oocyte will degenerate. The mature ovum has a diameter of about 0.2 mm.

In one embodiment, administration of progesterone after the follicle has reached a size of at least 15 mm induces LH surge independent of estradiol levels, leading to ovulation.

a. Monitoring Follicle Formation and Size

Monitoring follicle formation and size can be achieved using ultrasound imaging techniques. In one embodiment, the serial assessment of follicle number and size can be measured using ultrasound, commonly two-dimensional (2D) ultrasound. In such an embodiment, a subject's ovaries are subjected to 2D ultrasound. An observer such as a technician, nurse practitioner, or physician, etc. uses the 2D ultrasound images to identify and then systematically scroll through an ovary, measuring each follicle in turn.

In another embodiment, the serial assessment of follicle number and size can be measured using three-dimensional (3D) ultrasound. 3D ultrasound renders a volume rendering of ultrasound date. When generating a 3D volume the ultrasound data can be collected in four common ways. The first is freehand, which involves tilting the probe and capturing a series of ultrasound images and recording the transducer orientation for each slice. Second is mechanically, where the internal linear probe tilt is handled by a motor inside the probe. Third is using an endoprobe, which generates the volume by inserting a probe and then removing the transducer in a controlled manner. The fourth technology is the matrix array transducer that uses beamsteering to sample points throughout a pyramid shaped volume. In some embodiment, 3D ultrasound can be combined with automated software to count and measure follicles. Sono-AVC (automatic volume calculation: GE Medical Systems, Kretz, Austria) is a software program that identifies and quantifies hypoechoic regions within a 3D dataset and provides an automatic estimation of their absolute dimensions and volume (Raine Fenning et al., 2007a). Because each different volume is separately color coded, Sono-AVC is an ideal tool for studying follicular development in response to ovarian stimulation. SonoAVC provides highly reliable and valid measures of follicle diameter and volume.

In one embodiment, a subject's follicle development is measured by ultrasound beginning as early as 3 days following the start of her period. In other embodiment, the subject's follicle development is measured by ultrasound beginning 3 to 20 days following the start of her period. The subject's ovarian follicles can be measured daily, every other day, or every third day until the follicle is the appropriate size to begin progesterone treatment. In some embodiments, the subject receives her first intravaginal ultrasound on day 3, day 4, day 5, day 6, day 7, day 8, day 9, day 10, day 11, day 12, day 13, day 14, day 15, day 16, day 17, day 18, day 19 or day 20 following the start of her period.

2. Progesterone and Bioidentical Progesterone

In one embodiment, progesterone or bioidentical progesterone are administered to the subject to induce ovulation when the follicle has reached a size of at least 15 mm. The progesterone is able to trigger an LH surge and ovulation without the involvement of E2. Even in the early days of ovulation research, the role of the E2 as an ovulation trigger was questioned, when a sharp increase in circulating progesterone was detected as early as 12 hours before any changes in LH or E2 (Hoff at al, 1983). Progesterone has all the attributes of a perfect "witness" to the follicle's readiness (Zalányi 2001) because its changes are directly linked to the follicle's basement membrane disintegration, which signals the imminent rupture of the follicle. Further, unlike E2, the preovulatory progesterone remains relatively constant throughout follicular phase.

It has been shown that during the natural cycle progesterone rise to about 0.5 ng/ml preceding the LH, and E2 surge by about 12 hours, which makes progesterone the most upstream candidate for the chain of events leading to ovulation. Historically progesterone has been viewed as an ovulation blocking agent (Selye et al, 1936). This ability of progesterone is well known and is supported by vast experience with the variety of progestins in birth-control pills. At the first sight, this is irreconcilable with the possibility of progesterone causing LH to surge and induce ovulation. Particularly, because the circulating level of progestins used in birth-control formulations is considerably smaller than the preovulatory level of progesterone of 0.5 ng/ml.

The first crucial step in resolving this contradiction is recognizing that gonadotropin surge requires their accumulation within the respective granins during the preceding follicular phase. Without such accumulation, there is no surge. Second, as can be seen from the Table 1 the activity of progestins is considerably higher than that of progesterone. Therefore, comparing them to progesterone by the amount in the circulation is misleading. They should instead be compared by their activity instead. The estimated activity of all progestins formulation in the circulation is higher than an equivalent of 0.5 ng of preovulatory progesterone (Table 1).

TABLE 1

Consensus values of circulating progestins.

| Progestin | Consensus value (mg) |
|---|---|
| Norethindrone | 0.35 |
| D/L norgestrel | 0.075 |
| Medroxyprogesterone acetate | 5 |
| Dydrogesterone | 10 |

Consequently, at those levels, progestins would be expected to both, desensitize progesterone or perhaps by proxy also GnRH receptors, and/or continuously drain the pituitary of LH and FSH, interfering with their accumulation that is required for a surge. Thus, it can be inferred that when progesterone is very low, during the follicular phase, it allows LH to accumulate and receptors to become sensitized. As the result, when progesterone rises within a narrow window, of about 12 hrs preceding the LH surge, it causes LH to flare-up, leading to subsequent ovulation.

On the other hand, if progesterone activity is continuously present at the levels above its physiological pre-ovulatory level, such as the case with all birth control formulations, during pregnancy, or the luteal phase, it causes desensitization of its own or GnRH receptors (McArdle et al, 1995), so that LH accumulation or its surge are not possible, and ovulation is blocked.

In one embodiment, administration of progesterone or bioidentical progesterone induces LH surge and subsequently ovulation in a subject.

Bioidentical progesterone is a lab-made progesterone that is similar to endogenously produced progesterone. Bioidentical hormones are made from plant estrogens. In one embodiment, bioidentical progesterone is used in the disclosed methods and compositions.

i. Determining Target Progesterone Level

In one embodiment, the baseline circulating levels of progesterone are calculated before the subject is administered progesterone. Circulating levels of progesterone can be determined from a blood sample using methods known in the art. Such methods of determining levels of progesterone in circulation include but are not limited to immunoassays such as enzyme-linked immunosorbent assay (ELISA) and radioimmunoassay (RIA) using microarrays or chips, coated beads, glass fibers, or microcapillary discs, and radioreceptor assays (RRA).

In one embodiment, the baseline circulating levels of progesterone are used to determine the target maximum progesterone concentration for the subject. The target concentration is calculated by multiplying the baseline level by a number from 3 to 20.

Circulating levels of progesterone can be monitored throughout the entire controlled stimulation period, from the start of the menstrual period, through the administration of the triggering dose of progesterone, until ovulation has occurred.

3. Additional Therapeutics

In one embodiment, the methods and compositions disclosed herein can be used in combination with other infertility therapeutics and treatment methods to ensure the highest potential for successful ovulation, insemination, and viable pregnancy. Additional therapeutics that can be incorporated into the disclosed methods are described below.

i. Anti-Inflammatory Agents

In some embodiments, the female subjects are administered an anti-inflammatory agent before the administration of the trigger dose of progesterone to prevent premature rupture of the follicle. By preventing premature rupture of a follicle, the follicle can be safely taken to the size where it is large enough to rupture following progesterone injection. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

ii. Estrogen Modulators

In one embodiment, one or more estrogen modulator is administered to the subject prior to administration of the triggering dose of progesterone to induce ovulation. The estrogen modulators are administered to the subject for three to five days beginning on the 3rd to 5th days of the subject's menstrual period. In one embodiment, the estrogen modulator is administered to the female subject 3, 4, or 5 days after her menstrual period has begun. In another embodiment, the estrogen modulator is administered for 1, 2, 3, 4, or 5 days. Exemplary estrogen modulators include but are not limited to non-steroidal aromatase inhibitors and selective estrogen receptor modulators.

Non-steroidal aromatase inhibitors inhibit the conversion of androgens into estrogens by aromatase, thereby reducing the amount of estrogen in circulation. Non-steroidal aromatase inhibitors are useful for ovulation induction. Aromatase inhibitors increase ovarian sensitivity to FSH. Exemplary non-steroidal aromatase inhibitors include but are not limited to anastrozole and letrozole.

Selective estrogen receptor modulators are a class of drugs that act on the estrogen receptor. They are useful for the induction of ovulation. They have predominant antiestrogenic action resulting in long-lasting estrogen receptor depletion. Exemplary selective estrogen receptor modulators include but are not limited to triphenylethylenes such as clomiphene citrate, tamoxifen, and toremifene, and the benzothiophene, raloxifene.

iii. GnRH Antagonists

In one embodiment, one or more GnRH antagonists are administered to the subject before the subject is administered the triggering dose of progesterone. GnRH antagonists competitively and reversibly bind to GnRH receptors in the pituitary gland, blocking the release of luteinizing hormone (LH) and follicle-stimulating hormone (FSH) from the anterior pituitary. Administration of GnRH antagonists during the late-follicular phase effectively prevents a premature rise in serum luteinizing hormone (LH) levels in most women.

In one embodiment, the GnRH antagonists is administered to the female subject for at least one day before the triggering dose of progesterone is administered. The GnRH antagonist can be administered for 1, 2, 3, 4, or 5 days before the progesterone trigger dose is administered. In some embodiments, the GnRH antagonists is administered to the female subject the day before the triggering dose of progesterone is administered.

Exemplary GnRH antagonists include but are not limited to the peptide molecules abarelix, cetrorelix, degarelix, and ganirelix and the small-molecule compounds elagolix and relugolix.

C. Subjects to be Treated

In one embodiment, the disclosed methods and compositions are used to induce ovulation in subjects in need thereof. Female subjects in need of ovarian stimulation or ovulation induction can be trying natural impregnation, IVF, IUI, or frozen transfer cycle. In some embodiment, the female subject is a healthy subject.

In other embodiments, the female subject has an infertility problem, or has no diagnosed infertility problem but has historically had trouble naturally becoming pregnant. Causes for infertility or reduced infertility include but are not limited to ovarian disorders, endometriosis, poor egg quality, polycystic ovarian syndrome (PCOS), fallopian tube problems, unexplained infertility, poor sperm quality, age, and premature ovarian insufficiency. The disclosed methods and compositions can be used as part of IVF, IUI, natural cycle, or frozen transfer cycle.

1. Ovulation Disorders

Ovulation disorders occur when the female ovulates infrequently or not at all. They account for infertility in about 1 in 4 infertile couples. Problems with the regulation of reproductive hormones by the hypothalamus or the pituitary gland, or problems in the ovary, can cause ovulation disorders. In one embodiment, the disclosed methods and compositions can induce ovulation in women suffering from ovulation disorders. In such an embodiment, progesterone triggers ovulation in the woman and the egg can be harvested from IVF, IUI, or frozen transfer cycle, or the woman can attempt intercourse or natural insemination. Specific ovulation disorders are described below.

i. Polycystic Ovary Syndrome

Polycystic ovary syndrome (PCOS) causes a hormone imbalance, which affects ovulation. PCOS is often associated with insulin resistance and obesity, abnormal hair growth on the face or body, and acne. It's the most common cause of female infertility. In one embodiment, the methods and compositions disclosed herein can be used to induce ovulation in a female subject having PCOS. In such an embodiment, progesterone triggers ovulation in the subject, and the egg can be harvested from IVF. IUI, or frozen transfer cycle, or the woman can attempt intercourse or natural insemination.

ii. Hypothalamic Dysfunction

In another embodiment, the disclosed compositions and methods can be used to induce ovulation in female subjects having hypothalamic dysfunction. Hypothalamic dysfunction occurs when the production of FSH and LH are disrupted, leading to an imbalance in their levels and a failure to stimulate ovulation. Excess physical or emotional stress, a very high or very low body weight, or a recent substantial weight gain or loss can disrupt production of these hormones and affect ovulation. Irregular or absent periods are the most common signs of hypothalamic dysfunction. In one embodiment, the methods and compositions disclosed herein can be used to induce ovulation in a female subject having hypothalamic dysfunction. In such an embodiment, progesterone triggers ovulation in the subject, and the egg can be harvested from IVF, IUI, or frozen transfer cycle, or the woman can attempt natural insemination.

In another embodiment, triggering LH surge and ovulation using the disclosed methods and compositions can reset the functioning of the hypothalamus by resuming the natural balance of LH and FSH, and reduce or prevent future hypothalamic dysfunction in the subject iii. Premature Ovarian Failure In another embodiment, the disclosed methods and compositions can be used to trigger ovulation in subjects having premature ovarian failure. Premature ovarian failure, also called primary ovarian insufficiency, is usually caused by an autoimmune response or by premature loss of eggs from the ovary (possibly from genetics or chemotherapy). The ovary no longer produces many eggs, and it lowers estrogen production in women under the age of 40. In one embodiment, the methods and compositions disclosed herein can be used to induce ovulation in a female subject having early stage ovarian failure. In such an embodiment, progesterone triggers ovulation in the subject, and the egg can be harvested from IVF, IUI, or frozen transfer cycle, or the woman can attempt natural insemination.

iv. Prolactin Imbalance

One embodiment provides a methods of triggering ovulation in a subject having infertility problems due to too much prolactin. If the pituitary gland causes excess production of prolactin (hyperprolactinemia), estrogen production is consequently reduced, which may cause infertility. Usually related to a pituitary gland problem, this can also be caused by medications prescribed for another disease. In one embodiment, the methods and compositions disclosed herein can be used to induce ovulation in a female subject having prolactin imbalance. In such an embodiment, progesterone triggers ovulation in the subject, and the egg can be harvested from IVF, IUI, or frozen transfer cycle, or the woman can attempt natural insemination.

D. Pharmaceutical Compositions

Pharmaceutical compositions including progesterone or bioidentical progesterone with or without a delivery vehicle are provided. Pharmaceutical compositions can be formulated for administration by parenteral (intramuscular, intraperitoneal, intravenous (IV) or subcutaneous injection), enteral, or transmucosal (nasal, vaginal, rectal, or sublingual) routes of administration or using bioerodible inserts and can be formulated in dosage forms appropriate for each route of administration.

In certain embodiments, the compositions are administered locally, for example by a suppository inserted into the vagina. In some embodiments, the compositions are injected or otherwise administered directly into the vasculature onto vascular tissue at or adjacent to the intended site of treatment. Typically, local administration causes an increased localized concentration of the composition which is greater than that which can be achieved by systemic administration.

a. Formulations for Parenteral Administration

Pharmaceutical compositions including progesterone or bioidentical progesterone can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

b. Enteral Formulations

Pharmaceutical compositions including progesterone or bioidentical progesterone can be formulated for enteral administration. Suitable oral dosage forms of progesterone pharmaceutical compositions include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

c. Formulations for Vaginal Delivery

In another embodiment, the progesterone pharmaceutical composition is formulated for vaginal delivery. The vaginal drug delivery system provides a sustained delivery of progesterone or bioidentical progesterone to the vaginal epithelium for triggering ovulation. The delivery system can be a solid object delivery system such as a vaginal ring, pessary, tablet or suppository, for example. In another embodiment, the composition for vaginal delivery is a paste or gel having a sufficient thickness to maintain prolonged vaginal epithelium contact. In yet another embodiment, it can be a coating on a suppository wall or a sponge or other absorbent material impregnated with a liquid drug containing solution, lotion, or suspension of bioadhesive particles. Any form of drug delivery system which will effectively deliver the treatment agent to the vaginal endothelium is intended to be included within the scope of this invention. In a preferred embodiment, the vaginal delivery system for progesterone is a suppository drug delivery system. The vaginal delivery route of drugs through the vaginal mucosa to the uterus and/or to the general circulation is described, for example, in U.S. Pat. Nos. 6,086,909, 6,197,327 and 6,572,874.

d. Controlled Delivery Polymeric Matrices

The pharmaceutical compositions including progesterone disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of progesterone or bioidentical progesterone. These may be natural or synthetic polymers. Synthetic polymers typically have a better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl. Polymer Sci., 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

In one embodiment, the controlled release polymeric device releases a steady level of progesterone in an amount effective to maintain a progesterone plasma concentration between about 0.1 ng/ml to about 100 ng/ml for at least five days following administration or implantation of the device. In some embodiments, the device is an implantable polymeric rod that is inserted subcutaneously into the arm or leg of the subject or is implanted into the uterine lining of the subject. In another embodiment, the controlled release polymeric device can be a patch that is affixed to the skin to release progesterone over time.

EXAMPLES

Example 1. Case Study 1

Figure 4A:
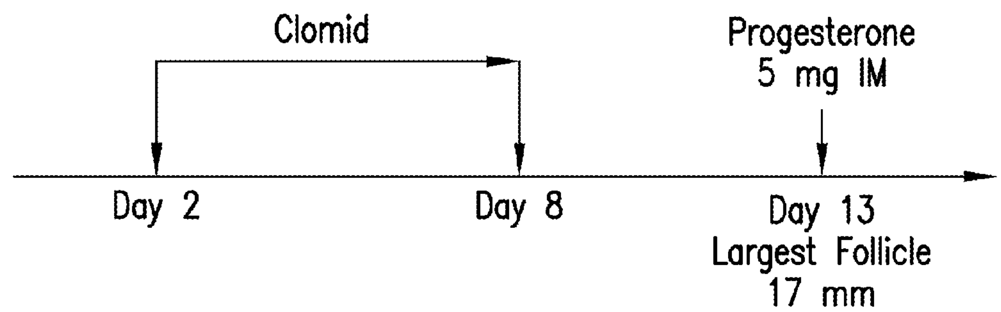
FIG. 4A is a schematic showing the treatment regimen for case report 1.
Figure 4B:
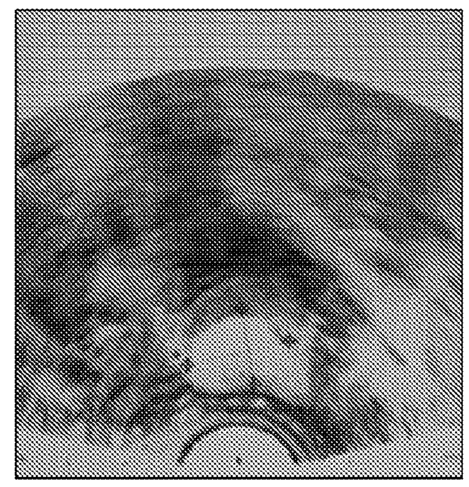
FIGS. 4B and 4C are ultrasound images of the ovarian follicle of the subject of case report 1.
Figure 4C:
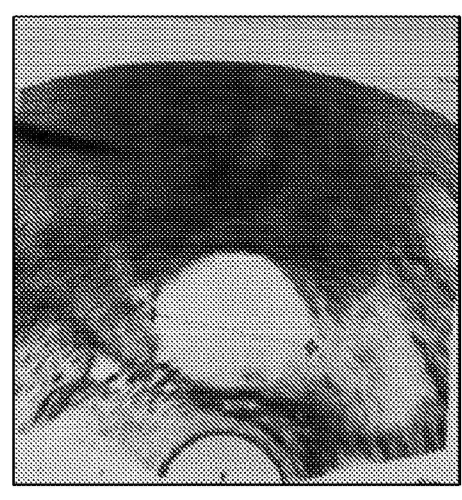

Materials and Methods:

A 35 years old woman, gravida 0, para 0, who failed to become pregnant following two previous natural IUI cycles with hCG as a trigger was suggested to have her ovulation triggered with progesterone. For the natural cycle, she was monitored with ultrasound at the base line on day 2, and then day 12 and 13. At day 13 of the cycle, her leading follicle had reached a size of 17 mm (FIG. 4B), P4 was 1.5 ng/ml and LH was 5 IU/L. She was given an intramuscular injection of 5 mg of progesterone. The protocol is outlined in FIG. 4A Results:

LH was at the ovulation level within 12 hrs, however, the follicle failed to rupture, and an active cyst has developed (FIG. 4C). Failure of the follicle to rupture was attributed to its size (17 mm) at the time of the trigger.

TABLE 2

Circulating hormone levels after trigger injection.

| | Time (hrs) | | | |
|---|---|---|---|---|
| Hormone | 0 | 10 | 49 | 96 |
| P4 | 1.55 | 14 | 8 | 43 |
| LH | 10.9 | 28.4 | 11.36 | |

Example 2. Case Study 2

Materials and Methods

Figure 5A:
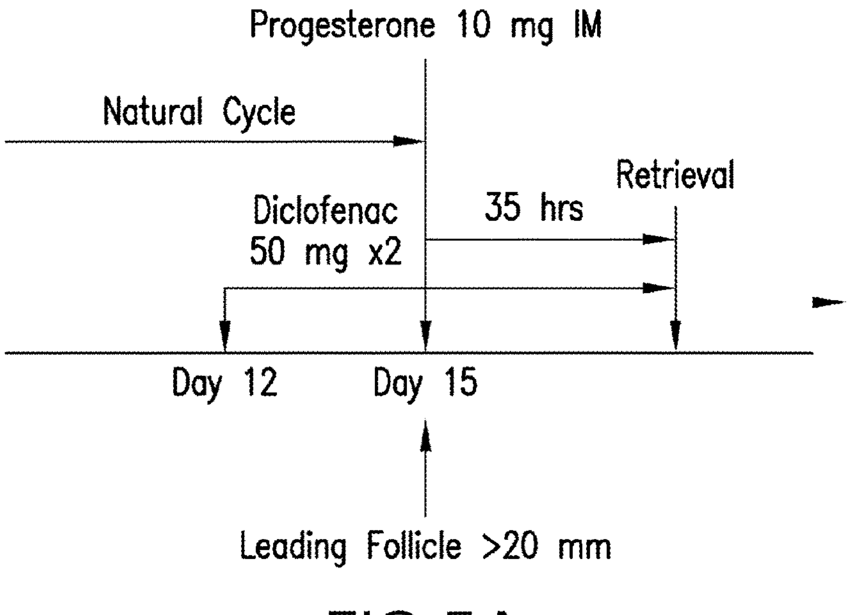
FIG. 5A is a schematic showing the treatment regimen for case report 2.

A 41 years old woman, gravida 0, para 0, interested only in a controlled natural IVF cycle. The treatment protocol is outlined in FIG. 5A.

Results

Figure 5B:
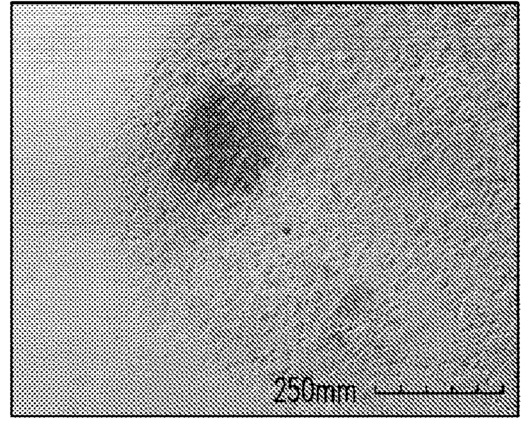
FIGS. 5B-5C are images of the egg that was retrieved following the treatment regimen.
Figure 5B:
Figure 5C:
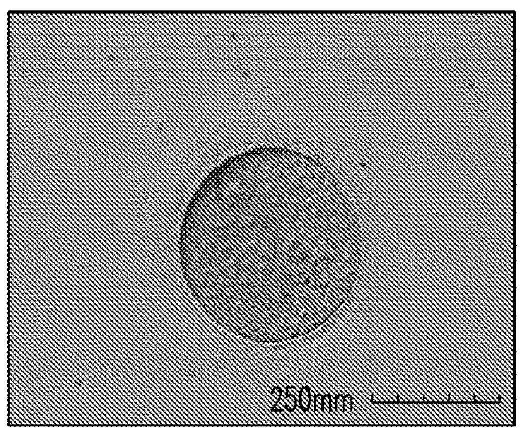

A single egg failed to become fertilized (FIGS. 5B-5C)

Example 3. Case Study 3

Materials and Methods

Figure 6A:
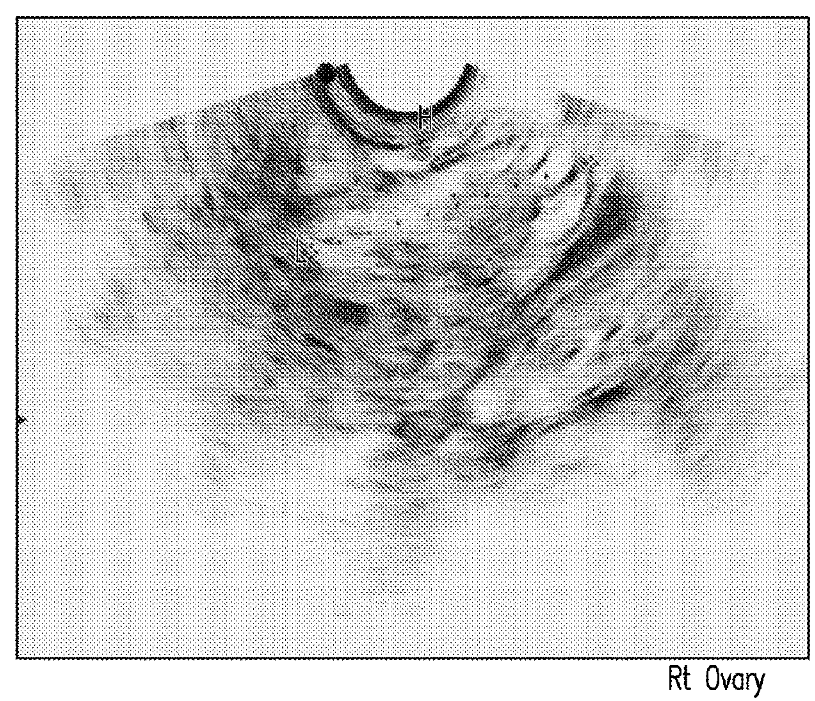
FIG. 6A-6B are ultrasound images of the left and right ovary, respectively, of the subject of case report 3.
Figure 6B:
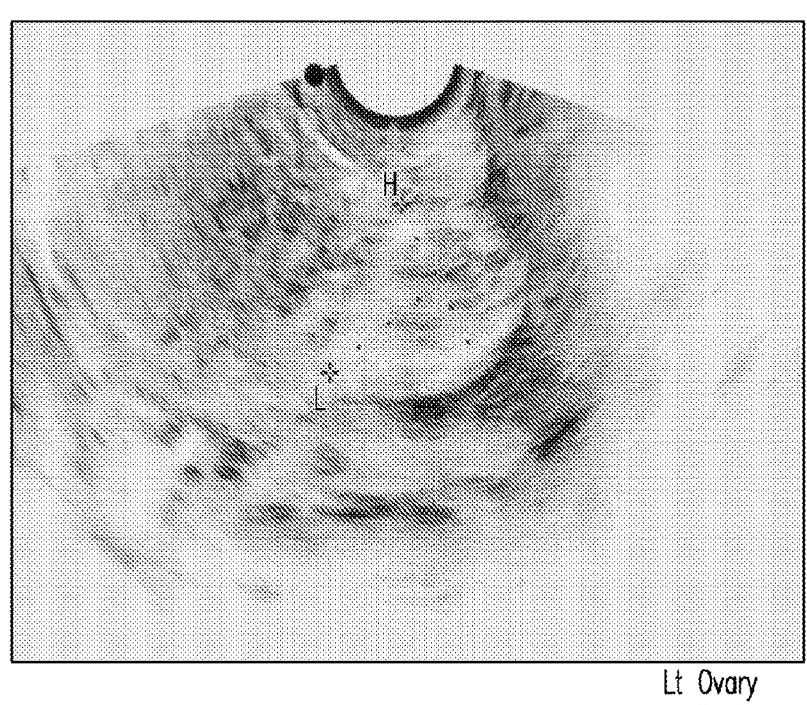
Figure 6C:
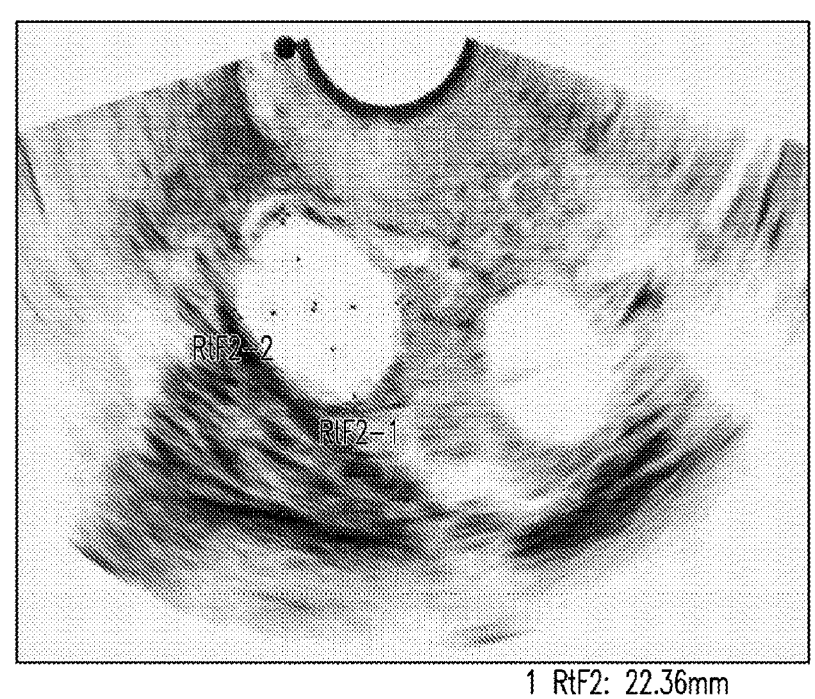
FIGS. 6C-6D are ultrasound images of leading follicles in the right ovary before the trigger shot.
Figure 6D:
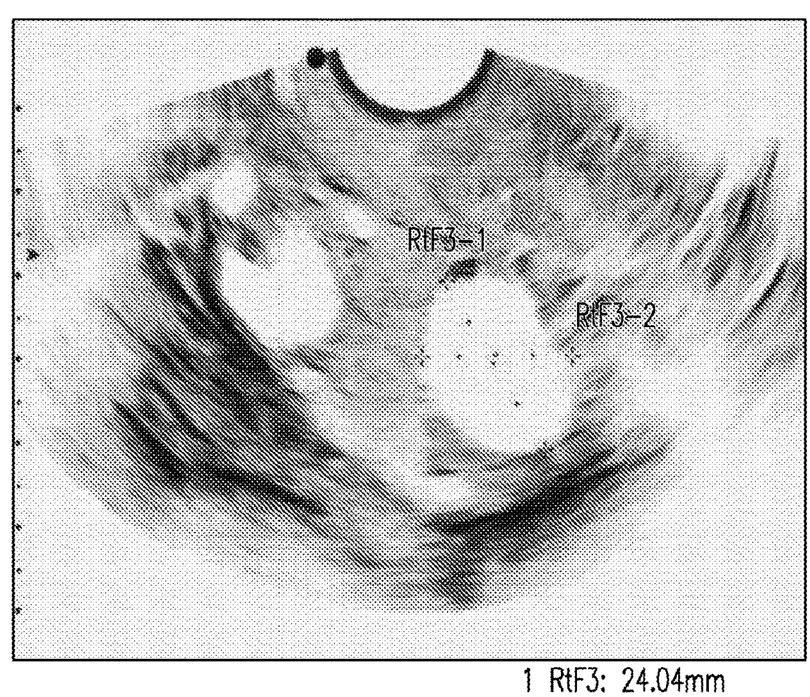
Figure 6E:
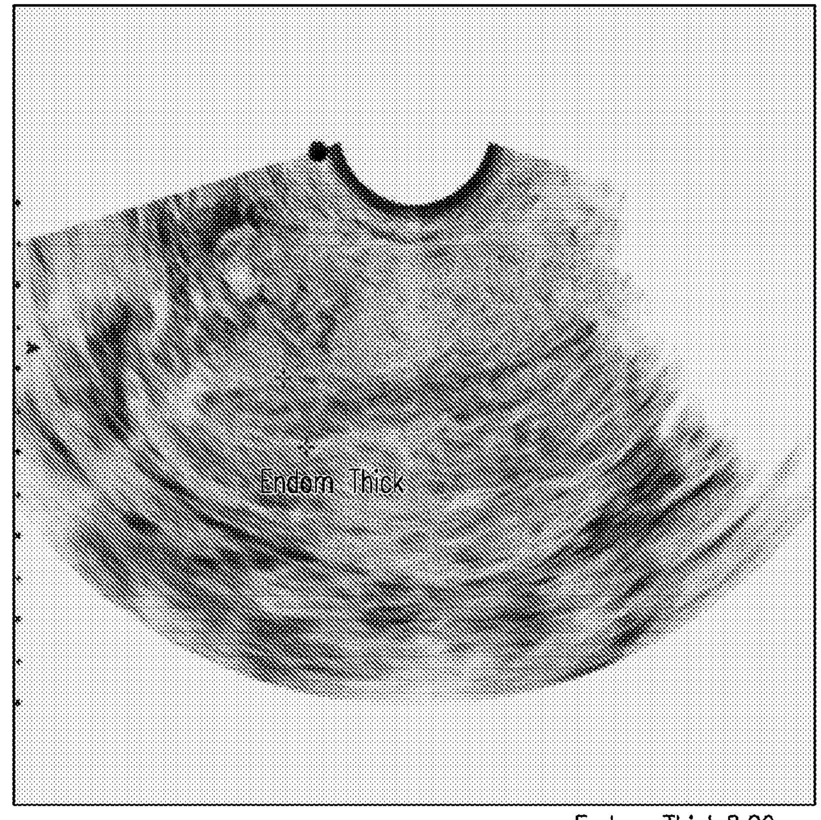
FIG. 6E is an ultrasound image of the uterine lining before the trigger shot.

A 30 years old female, G2 P1, SAB1, height 152 cm, weight 164 lb was referred for infertility treatment following 6-month inability to conceive naturally. Patient's medical history was significant for PCOS and subclinical hypothyroidism, for which she was taking levothyroxine 100 cmg. Patient had menarche at 12, average period duration of 45 days, average menses duration of 6 days. Patient's fallopian tubes were both patent per HSG, with a normal uterine cavity (FIG. 6E). Her AMH was 9.3 ng/ml.

In the first controlled stimulation cycle, the patient received 100 mg Clomiphene citrate (CC) for 5 days starting on the 5th day of her period. She was triggered on day 19 following the first dose of CC, when she had a single 22 mm follicle and her E2, LH and P4 were 400 pg/ml, 38 mIU/ml and 0.73 ng/ml respectively. The additional luteal phase support was initiated on day 3 after the trigger shot with 10,000 IU of Novarel, followed by daily suppositories with 200 mg of progesterone by suppositories. Patient's hCG 2 weeks post trigger was negative, which was not completely surprising since her LH on the day of the trigger was within post ovulatory range, indicating that spontaneous LH surge has taken place prior to the time of the trigger shot.

In the second controlled stimulation cycle, the patient received 5 mg of Letrozole in addition to 100 mg Clomiphene citrate (CC) for 5 days starting on the 3rd day of her period. For two days before the trigger shot patient received 50 mg of Diclofenac as suppositories. She was triggered on day 16 following the first dose of CC, when she had two follicles in her left ovary (25 mm and 18 mm) and three follicles in the right ovary (23 mm, 12 mm and 12 mm). The additional luteal phase support was initiated on day 3 after the trigger shot by daily suppositories with 200 mg of progesterone. Patient's hCG 2 weeks post trigger was 178 and increased to 1459 four days later. No fetal heart beat was observed on the ultrasound two and four weeks later, and a dilation and curettage was performed.

The medication regiment, at the beginning of the third attempt was the same as in the previous attempt when the patient became pregnant with 5 mg of Letrozole in addition to 100 mg CC for 5 days starting on the 3rd day of her period. On day 13 of the stimulation patient received one suppository with 50 mg of Diclofenac and one injection of Citrotide to prevent premature luteinization. The following day she was triggered with a single injection of 5 mg of progesterone in oil. Before the trigger her P4 and LH were 0.62 ng/ml and 4.26 IU/L respectively (Table 3) and ultrasound identified three follicles 22, 22 and 19 mm (FIG. 6C-6D).

Figure 6F:
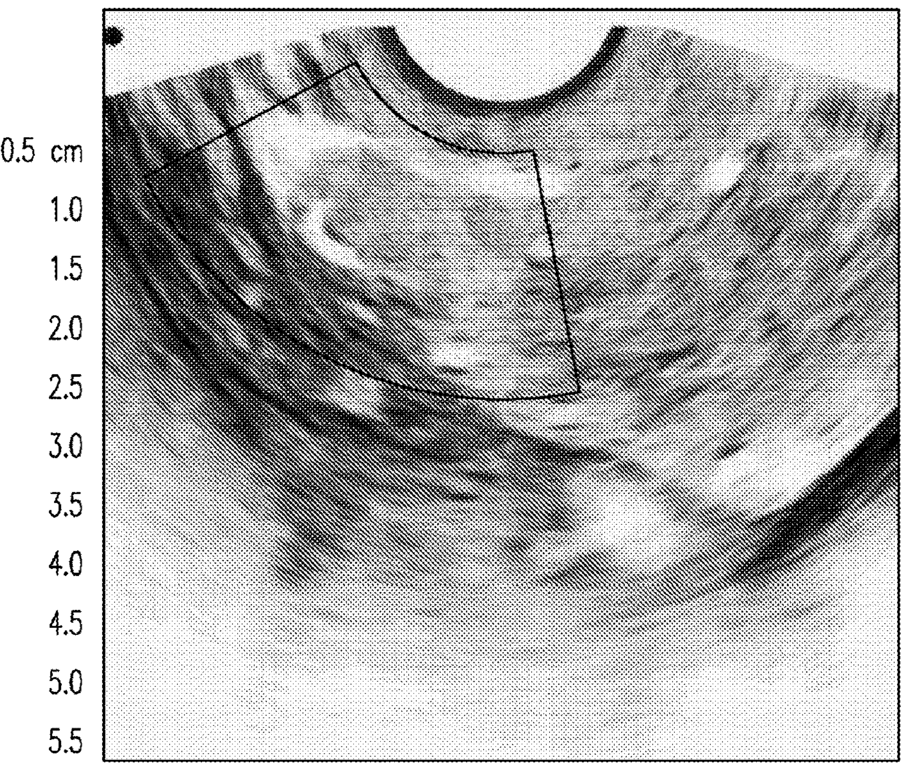
FIGS. 6F-6G are ultrasound images of ruptured follicles after the trigger shot.
Figure 6G:
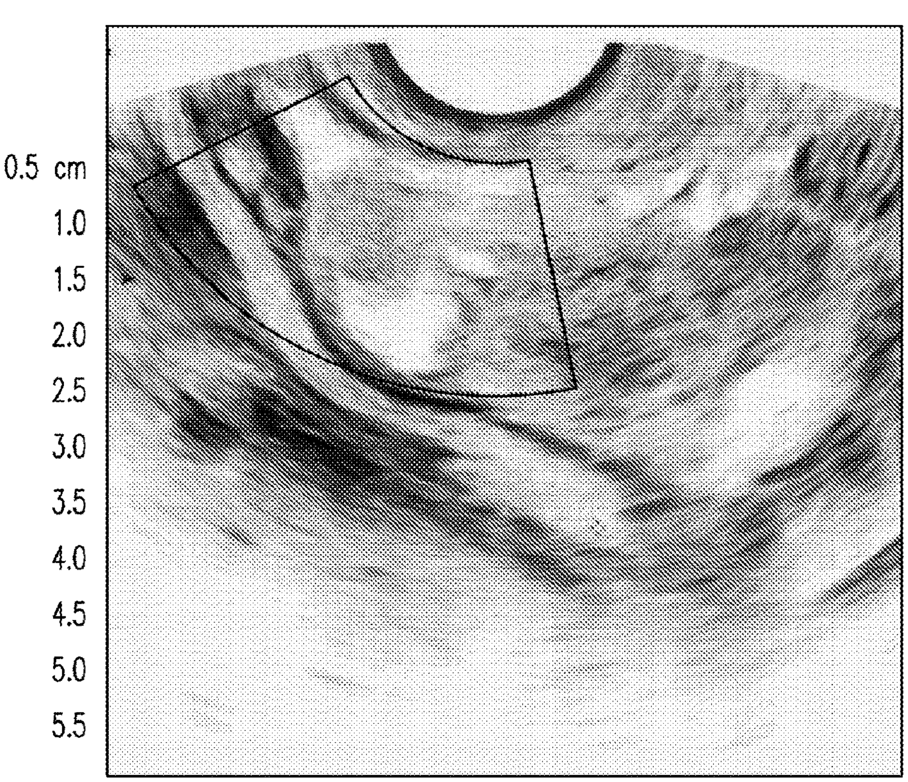
Figure 6H:
FIG. 6H is an ultrasound image of the uterine lining after the trigger shot.
Figure 6I:
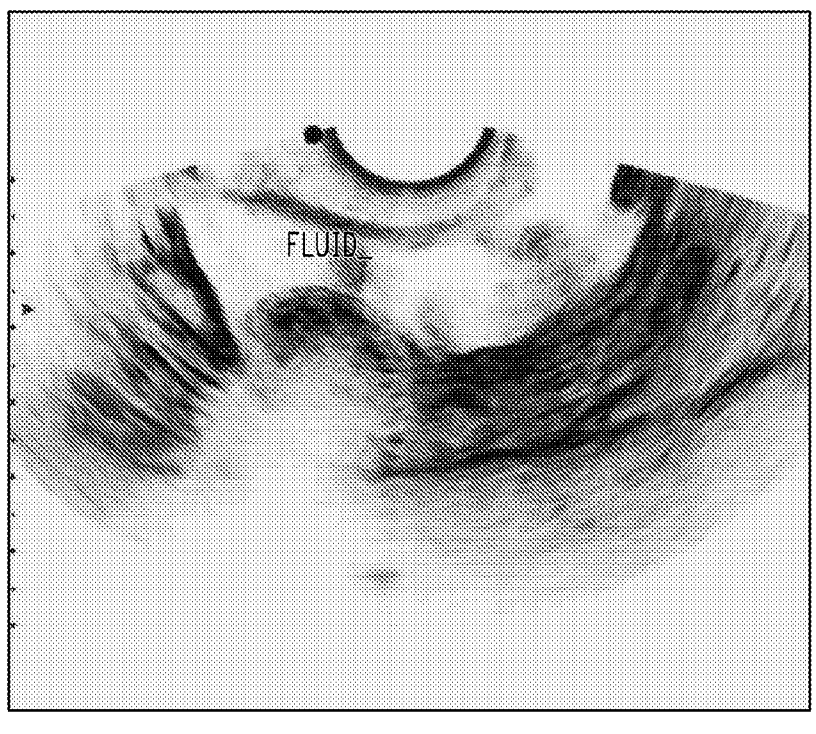
FIG. 6I is an ultrasound image showing fluid behind the uterus.

Seventeen hours after that P4 and LH rose to 8.01 ng/ml and 37.01 IU/L respectively, indicating gonadotropin surge has taken place. The ultrasound performed on day 3 following the trigger shot confirmed that all three follicles ruptured (FIGS. 6F-6G). Patient had fluid behind the uterus (FIG. 6I)—a classic hallmark of ovulation. Seven days after the trigger shot, P4 level was 38.39 ng/ml at which time the patient was started on 200 mg progesterone vaginal suppository daily. The patient had her period 2 weeks later indicating that no pregnancy occurred.

TABLE 3

Ultrasound, P4 and LH results before and after trigger shot with progesterone.

| | Ultrasound observation | P4 (ng/ml) | LH (IU/L) |
|---|---|---|---|
| Baseline | Clear, no cyst (FIGS. 10A-10B) | 0.4 | Not measured |
| First follicular ultrasound | 2 leading follicles, 14 mm and 13 mm. Lining 6.5 mm | 0.49 | 9.47 |
| Stimulation day 10 | 2 follicles leading 17 mm and 16 mm. | 0.38 | 5.09 |
| Stimulation day 12 Day of a progesterone trigger shot | 2 leading follicles 22 mm each and 19 mm (FIGS. 10C-10D) Uterine lining 8.8 mm (FIG. 11) | 0.62 | 4.26 |
| 17 hours 30 minutes after trigger shot | Not performed | 8.01 | 37.01 |
| Day 3 after trigger shot | Fluid behind uterus (FIG. 12D); all follicles ruptured (FIGS. 12A-12B); Uterine lining - 15.2 mm (FIG. 12C) | Not measured | Not measured |
| 7 days after trigger shot | Not performed | 38.39 | Not measured |

The lowest dose of progesterone reported for induction of a gonadotropins surge is 10 mg injected intramuscularly (Leyendecker, et al, 1972). In case report 3, an injection of only 5 mg of progesterone was used, since in the first attempt, this patient had an apparent spontaneous LH surge at the progesterone level of 0.63 ng/ml, consistent with the previous report of an average triggering progesterone level in the circulation of 0.5 ng/ml (Hoff, Quigley, and Yen 1983).

Consequently, the target cumulative progesterone level in circulation was 1 ng/ml. Based on pharmacodynamics of progesterone (Leyendecker, et al, 1972), it was estimated that in order to achieve circulating progesterone level at its peak (120 minutes post injection) 1 ng/ml, an additional 0.35 ng/ml was needed to add to the patient's own 0.63 ng/ml. This would be achieved with about 5 mg of progesterone in sesame oil for intramuscular injection.

The results show that injection of 5 mg of progesterone has indeed resulted in the surge of LH, rupture of all three follicles and appearance of fluid behind the uterus—all classical hallmarks of ovulation. Furthermore, progesterone continued to rise to the expected level several days later. The patient's P4 level on day 5 post trigger was excellent and additional supplementation with progesterone thereafter was given only for an abundance of caution.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of triggering ovulation in a subject in need thereof comprising, (i) monitoring ovarian follicle development and size during the follicular phase of the menstrual cycle in the subject; and (ii) when the follicle reaches a size of at least 15 mm, administering to the subject a pharmaceutical composition comprising progesterone, bioidentical progesterone, or progestin in an amount effective to increase the plasma concentration of progesterone in the subject to a level of about 0.1 ng/ml-100 ng/ml, wherein the subject is a human.

2. The method of claim 1, wherein the pharmaceutical composition is formulated for oral, intravenous, subcutaneous, intramuscular, transvaginal, or rectal administration.

3. The method of claim 2, wherein the amount of progesterone in the pharmaceutical composition formulated for oral administration is between about 5 mg to about 30 mg.

4. The method of claim 2, wherein the amount of progesterone in the pharmaceutical composition formulated for intramuscular administration is between about 1 mg to about 3 mg.

5. The method of claim 1, wherein the administration of progesterone to the subject induces luteinizing hormone (LH) surge and ovulation in the subject.

6. The method of claim 1, further comprising repeating administration of progesterone to the subject several times over a period of about 4 hours to about 12 hours.

7. The method of claim 1, further comprising determining the subject's baseline plasma progesterone concentration prior to administering progesterone.

8. The method of claim 7, wherein the baseline plasma progesterone concentration is used to calculate the target maximum progesterone concentration for the subject, wherein the target concentration is calculated by multiplying the baseline level by a number from 3 to 20.

9. The method of claim 1, further comprising administering secondary fertility therapeutics to the subject.

10. The method of claim 1, further comprising administering an amount of progesterone to the subject daily for at least one day following the initial administration of progesterone.

11. The method of claim 1, wherein the subject in need thereof has infertility or reduced infertility caused by ovulation problems, endometriosis, poor egg quality, polycystic ovarian syndrome (PCOS), fallopian tube problems, unexplained infertility, poor sperm quality, age, or premature ovarian insufficiency.

12. The method of claim 1, wherein in step (ii), the plasma concentration of progesterone in the subject is increased to a level of about 0.1 ng/ml-1.0 ng/ml.

13. The method of claim 1, further comprising after step (ii), (a) measuring a luteinizing hormone (LH) surge in the subject.

14. The method of claim 1, wherein the subject is undergoing in vitro fertilization cycle (IVF).

15. The method of claim 1, wherein the subject is undergoing intrauterine insemination (IUI).

16. The method of claim 1, wherein the subject is undergoing timed intercourse.

17. The method of claim 1, further comprising, after step (ii), (b) harvesting egg(s) from the subject.

18. The method of claim 17, further comprising, after step (b), (c) performing in vitro fertilization (IVF) or intracytoplasmic sperm injection (ICSI).

19. The method of claim 18, further comprising, after step (c), (d) implanting the egg(s) into the uterus of the subject or a uterus of a different subject.

20. The method of claim 19, wherein step (d) is performed immediately after the IVF or ICSI.

21. The method of claim 19, wherein step (d) is performed the day after IVF or ICSI, and wherein the egg(s) is fertilized.

22. The method of claim 19, wherein step (d) is performed in the next cycle, and wherein the egg(s) is fertilized.

23. The method of claim 1, further comprising, before or concurrently with step (ii), (e) administering estradiol to the subject.

* * * * *